United States Patent
Koulikov

(10) Patent No.: US 9,989,729 B2
(45) Date of Patent: Jun. 5, 2018

(54) ULTRA STABLE RESONANT CAVITY FOR GAS ANALYSIS SYSTEMS

(71) Applicant: LI-COR, Inc., Lincoln, NE (US)

(72) Inventor: Serguei Koulikov, Los Altos, CA (US)

(73) Assignee: LI-COR, Inc., Lincoln, NE (US)

( * ) Notice: Subject to any disclaimer, the term of this patent is extended or adjusted under 35 U.S.C. 154(b) by 0 days. days.

(21) Appl. No.: 14/847,977

(22) Filed: Sep. 8, 2015

(65) Prior Publication Data

US 2016/0069795 A1 Mar. 10, 2016

Related U.S. Application Data

(60) Provisional application No. 62/047,394, filed on Sep. 8, 2014.

(51) Int. Cl.

| | | |
|---|---|---|
| *G01N 21/00* | (2006.01) | |
| *G02B 7/18* | (2006.01) | |
| *H01S 3/00* | (2006.01) | |
| *G02B 17/00* | (2006.01) | |
| *G01N 21/03* | (2006.01) | |

(Continued)

(52) U.S. Cl.

CPC ........... *G02B 7/181* (2013.01); *G01N 21/031* (2013.01); *G01N 21/39* (2013.01); *G02B 17/004* (2013.01); *H01S 3/0071* (2013.01); *G01N 21/3151* (2013.01)

(58) Field of Classification Search
CPC .. G01N 21/031; G01N 21/3151; G01N 21/39; G01N 21/3586; G01N 21/77; G01N 21/88; G01N 23/20; G01N 27/60; G01N 33/02; G02B 17/004; G02B 7/181;
(Continued)

(56) References Cited

U.S. PATENT DOCUMENTS

| | | | |
|---|---|---|---|
| 4,224,579 A * | 9/1980 | Marlett | H01S 3/031 372/33 |
| 4,784,468 A | 11/1988 | Van Wagenen et al. | |

(Continued)

FOREIGN PATENT DOCUMENTS

| | | |
|---|---|---|
| WO | WO 97/49983 A1 | 12/1997 |
| WO | WO 2005/108939 A1 | 11/2005 |
| WO | WO 2006/114635 A2 | 11/2006 |

OTHER PUBLICATIONS

Emsley, Matthew K., "Silicon Substrates with Buried Distributed Bragg Reflectors for Resonant Cavity-Enhanced Optoelectronics", IEEE Journal of Selected Topics in Quantum Electronics, vol. 8, No. 4, Jul./Aug. 2002.

(Continued)

*Primary Examiner* — Tri T Ton
(74) *Attorney, Agent, or Firm* — Leydig, Voit & Mayer, LLP; Gerald T. Gray

(57) ABSTRACT

Systems and methods for detecting trace gases utilize a resonance optical cavity and a coherent light source coupled to the cavity through a cavity coupling mirror. The cavity is constructed of a material having the same or a similar coefficient of thermal expansion as the mirror elements defining the cavity. The main (bulk) cavity material may be the same as the main (bulk) material that forms the mirror elements, or it may be different. Such resonant cavity configurations provide improved accuracy and stability as compared to existing cavity configurations based upon similar principles.

10 Claims, 4 Drawing Sheets

(51) Int. Cl.
*G01N 21/39* (2006.01)
*G01N 21/31* (2006.01)

(58) Field of Classification Search
CPC ......... H01S 3/0071; G01M 3/00; G01M 3/38; G06K 7/12
USPC .................................................. 356/432–444
See application file for complete search history.

(56) References Cited

U.S. PATENT DOCUMENTS

| | | | |
|---|---|---|---|
| 5,311,529 A * | 5/1994 | Hug | ...................... H01S 3/0323 372/107 |
| 5,528,040 A | 6/1996 | Lehmann et al. | |
| 6,075,252 A | 6/2000 | Atkinson et al. | |
| 7,113,286 B2 | 9/2006 | Yan | |
| 7,695,680 B2 | 4/2010 | Unlu et al. | |
| 7,864,326 B2 | 1/2011 | Cox et al. | |
| 8,040,518 B2 | 10/2011 | Tuchman et al. | |
| 8,154,727 B2 | 4/2012 | Dreyer et al. | |
| 8,198,590 B2 | 6/2012 | Cox et al. | |
| 2003/0189711 A1 * | 10/2003 | Orr | .......................... G01J 3/42 356/484 |
| 2005/0062972 A1 | 3/2005 | Krusen | |
| 2005/0094158 A1 | 5/2005 | Paldus et al. | |
| 2005/0134836 A1 | 6/2005 | Paldus et al. | |
| 2006/0123884 A1 * | 6/2006 | Selker | ................ G01N 21/1702 73/24.02 |
| 2007/0133001 A1 | 6/2007 | Cox | |
| 2010/0277737 A1 | 11/2010 | Tuchman et al. | |
| 2011/0214479 A1 * | 9/2011 | Kachanov | .......... G01N 21/1702 73/24.02 |
| 2011/0214480 A1 | 9/2011 | Kachanov et al. | |

OTHER PUBLICATIONS

Kachanov, A. et al., "Cavity-Enhanced Optical Feedback-Assisted Photo-Acoustic Spectroscopy with a 10.4 μm External Cavity Quantum Cascade Laser", Applied Physics B, Lasers and Optics, Jan. 2013, vol. 110, Issue 1, pp. 47-56.
Ma, Q., et al., "Trace Gas Detection Utilizing Optical Spectroscopy of Microresonant Cavities", AIAA Aerospace Sciences Meeting, Reno, Nevada, Jan. 8-11, 2007.
Sadeghi, N. et al., "Cavity Ring Down Spectroscopy Applied to Plasma Diagnosis".
International Preliminary Report on Patentability issued in International Application No. PCT/US2015/048994, dated Mar. 23, 2017.
International Search Report and Written Opinion issued in International Application No. PCT/US2015/048994, dated Dec. 7, 2015.
European Search Report dated Feb. 13, 2018, Application No. 15840262.8.

* cited by examiner

ULTRA STABLE RESONANT CAVITY FOR GAS ANALYSIS SYSTEMS

CROSS-REFERENCE TO RELATED APPLICATIONS

This patent application claims the benefit of U.S. Provisional Patent Application No. 62/047,394, filed Sep. 8, 2014, which is incorporated herein by reference.

This invention was made with government support under Grant Number DE-SC0009530 awarded by the Department of Energy. The government has certain rights in the invention.

BACKGROUND

The present disclosure relates to gas analysis systems and devices and more particularly to apparatus with reduced temperature sensitivity for measuring concentrations of gases.

SUMMARY

The present disclosure provides systems and methods for detecting trace gases according to various embodiments which utilize a resonance optical cavity and a coherent light source coupled to the cavity through a cavity coupling mirror. The cavity is constructed of a material having the same or a similar coefficient of thermal expansion as the mirror elements defining the cavity. For example, the main (bulk) cavity material may be the same as the main (bulk) material that forms the mirror elements, or it may be different. Such resonant cavity configurations provide improved accuracy and stability as compared to existing cavity configurations based upon similar principles. The various elements may include other materials, e.g., coatings and the like to enhance other properties of the system.

Embodiments advantageously reduce the temperature sensitivity of the apparatus and reduce mechanical stresses caused by ambient temperature variations.

According to one embodiment, an apparatus for detecting one or more analyte species present in a gaseous or liquid medium is provided. The apparatus typically includes a resonant optical cavity body structure made of a first material, the resonant optical cavity structure having a first end and a second end. The first material may include a glass or a glass ceramic. The resonant optical cavity body structure typically includes an inlet port for receiving a liquid or gaseous medium, and also an outlet port to allow the medium to exit the cavity. The apparatus also typically includes a first mirror element proximal to the first end of the optical cavity body structure, and a second mirror element proximal to the second end of the optical cavity body structure, wherein the first and second mirrors are each made of the first material or a material having the same or a substantially similar coefficient of thermal expansion as the first material. In certain aspects, the first material comprises fused silica. In certain aspects, the apparatus further includes a third mirror element proximal to the first or the second end, wherein the third mirror element is made of the first material or a material having the same or a substantially similar coefficient of thermal expansion as the first material. In certain aspects, the apparatus further includes a fourth mirror element proximal to the first or the second end, wherein the fourth mirror element is made of the first material or a material having the same or a substantially similar coefficient of thermal expansion as the first material. In certain aspects, the cavity is enclosed within or contained within a housing structure or chamber which allows for a controlled (e.g., pressure and/or temperature) environment for components contained within the housing structure or chamber.

According to another embodiment, a resonant optical cavity for use in an apparatus for detecting one or more analyte species present in a gaseous or liquid medium is provided. The resonant optical cavity typically includes a housing structure made of a first material, the housing structure having a first end and a second end, a first mirror element proximal to the first end of the housing structure, and a second mirror element proximal to the second end of the housing structure, wherein the first and second mirrors are each made of the first material or a material having the same or a substantially similar coefficient of thermal expansion as the first material. In certain aspects, the first material comprises fused silica. In certain aspects, the resonant optical cavity further includes a third mirror element proximal to the first or the second end, wherein the third mirror element is made of the first material or a material having the same or a substantially similar coefficient of thermal expansion as the first material. In certain aspects, the resonant optical cavity further includes a fourth mirror element proximal to the first or the second end, wherein the fourth mirror element is made of the first material or a material having the same or a substantially similar coefficient of thermal expansion as the first material. In certain aspects, the resonant optical cavity is enclosed within or contained within an external housing structure or chamber which allows for a controlled (e.g., pressure and/or temperature) environment for components contained within the external housing structure or chamber.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

Figure 1:
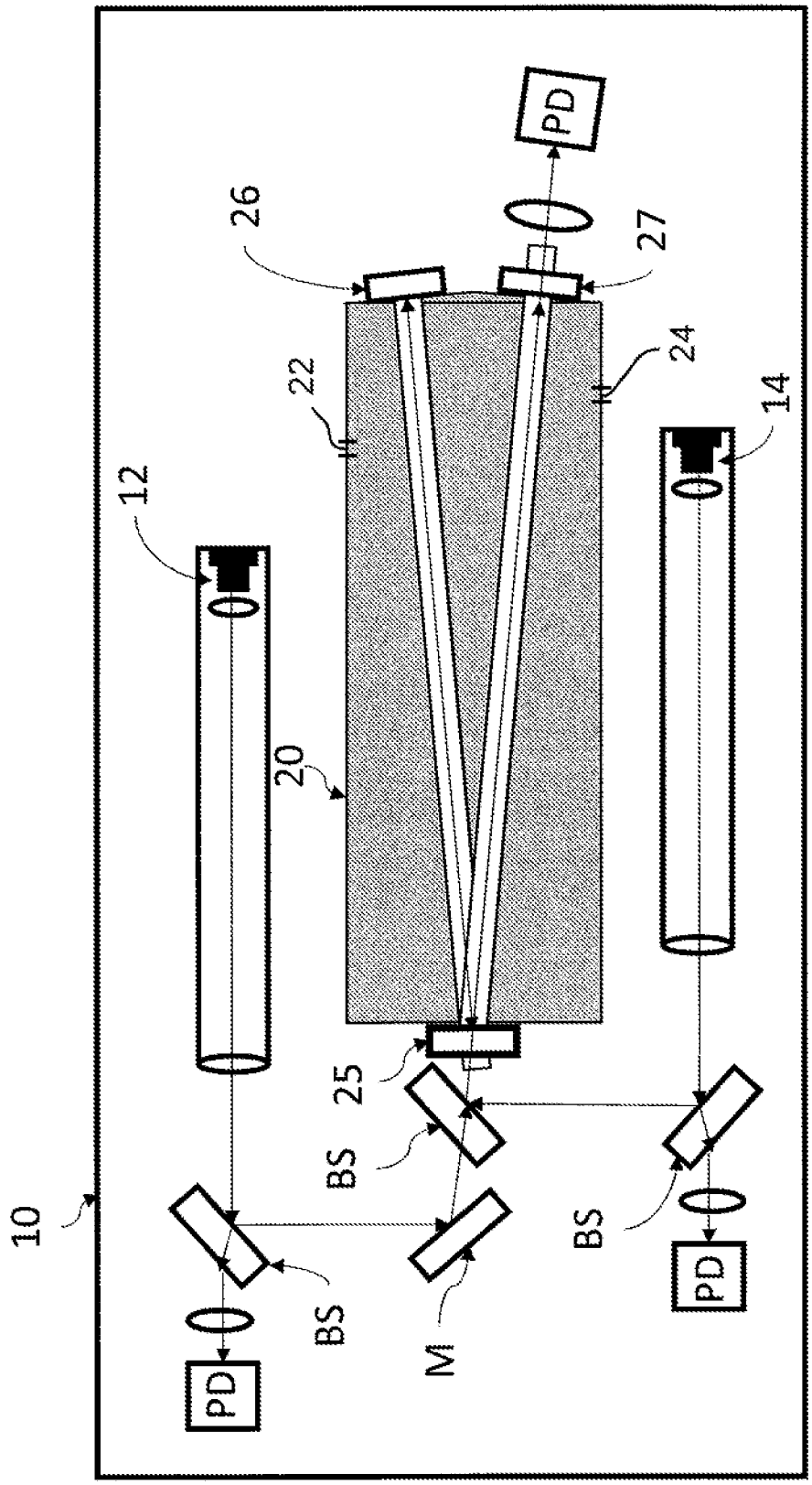
FIG. 1 shows an apparatus configuration according to an embodiment

The present disclosure relates generally to trace gas detection and more specifically to resonant optical cavities and cavity enhanced absorption spectroscopy systems and methods using the same. Such systems and methods are useful for measuring components of gas mixtures, such as trace gases in air. Embodiments advantageously reduce the temperature sensitivity of the apparatus and reduce mechanical stresses caused by ambient temperature variations.

Systems and methods for detecting trace gases according to various embodiments utilize a resonance optical cavity and a coherent light source coupled to the cavity through a cavity coupling mirror. The cavity is constructed of a material having the same or a similar coefficient of thermal expansion as the mirror elements defining the cavity. For example, the main (bulk) cavity material may be the same as the main (bulk) material that forms the mirror elements, or it may be different. Such resonant cavity configurations provide improved accuracy and stability as compared to existing cavity configurations based upon similar principles.

As will be appreciated, the terms "cavity," "optical cavity," "resonant optical cavity" and the like may be used interchangeably herein.

In certain embodiments, an apparatus includes a resonant optical cavity, including high reflectivity mirrors coupled with or mounted on or to a gas-containing cell, or a housing or body structure. Typically, high reflectivity mirrors are made from glass substrates with dielectric reflective coatings on them to provide high reflectivity for specific wavelengths or wavelength ranges. One useful material used to make mirror substrates is fused silica, which has a very low thermal expansion coefficient. At the same time, gas cell bodies are typically made from metals, which may not match the thermal expansion characteristics of the mirror elements. Very often the gas cell bodies are made from stainless steel. In some applications, low thermal expansion materials such as Invar may be used.

In certain embodiments, a resonant optical cavity body structure is provided with the same materials (e.g., fused silica) used for both the high reflectivity mirrors and the gas cell body to reduce a mechanical stress in the resonant optical cavity when it is exposed to different temperatures (e.g., a temperature gradient). In certain embodiments, different materials having the same or similar thermal expansion characteristics (e.g., same or substantially similar thermal expansion coefficient) are used for the high reflectivity mirrors and the gas cell body to reduce or minimize mechanical stress due to temperature differences. Similar or substantially similar thermal expansion coefficients will have values within about $10^{-6}$ m/m K (examples include quartz—Sitall, glass—Kovar). For example, both the high reflectivity mirrors and the gas cell body in the embodiments herein can be made from fused silica or other glass material having a low thermal expansion coefficient, e.g., less than about $3 \times 10^{-6}$ m/m K. For embodiments where the same material is used for both the high reflectivity mirrors and the gas cell body, the temperature-induced stress can be rather small. If materials with a low thermal expansion coefficient are used for the cavity body and mirrors, the resonant cavity is much less sensitive to temperature variations.

The mirrors are typically high-reflectivity mirrors, each having a reflectivity of about 99% or greater (for certain wavelengths or wavelength ranges) on a surface facing an inside of the cavity body structure. In certain aspects, the reflectivity of the mirrors is greater than about 99.9%, or even 99.99%. Additional mounting components may be made of the same or different materials as the mirror elements.

Additional useful materials for the mirrors and/or the cavity body structure include Corning ULE® 7972 titania-silicate glass and Schott ZERODUR glass ceramic.

FIG. 1 shows an exemplary cavity enhanced optical spectroscopy (CEOS) system 10 according to one embodiment. CEOS system 10 includes a dual laser, single resonant cavity configuration for measurement of trace gases in air, according to an embodiment. CEOS system 10 is particularly useful for measuring multiple, e.g., 3 different, trace gases. Both the resonant cavity 20 and high reflectivity mirrors 25 are made of the same material (e.g., fused silica). The design using fused silica was successfully implemented in a prototype. In certain embodiments, at least one of the folding mirrors and/or at least one of the beam shaping optical elements can also be made from the same material (or with a material with similar thermal expansion characteristics) as the mirrors and cavity, e.g. fused silica.

CEOS system 10 includes a first light source 12 and a second light source 14, each of which emits continuous wave coherent light, such as continuous wave laser light, and an optical cavity 20. A detector system (including one or more photodetectors "PD") is provided and configured to measure absorption within the cavity, and hence an absorption coefficient, as well as other characteristics of incident and/or reflected light. In one embodiment, the detector system includes one or more detectors (PD) configured and arranged to measure optical signal emerging from one or more of the cavity mirrors. As shown, cavity 20 is a V-shaped cavity defined by cavity coupling mirror 25 and mirrors 26 and 27. One or more optical components (M) are configured and arranged to facilitate directing, and mode matching laser light from sources 12 and 14 to the optical cavity 20 via cavity coupling mirror 25. Optional beam splitting elements (BS) may be included. Cavity coupling mirror 25, in one embodiment, is arranged at an angle with respect to one or both incident source. A portion of incident light from each source enters cavity 20 via mirror 25. Depending on the frequency of incident light and the optical length of cavity 20 (e.g., optical length from mirror 27 to mirror 25 to mirror 26), light circulating in the cavity 20 may build up and resonate at one or a plurality of cavity modes (cavity resonances evenly separated in frequency; commonly known as the FSR or free spectral range of the cavity). A small portion of the intracavity light circulating in cavity 20 between mirror 27, 25 and 26, emerges or escapes via mirror 27 and also mirrors 26 and 25 as determined by their transmissivity. The light escaping mirror 25 is controlled by the various mirrors (M) and other optical elements to pass back to the sources 12 and 14, e.g., for optical feedback. In certain aspects, light returning to sources may pass through optional phase control and/or attenuation elements, which advantageously provides for phase and/or intensity control of the optical feedback provided to sources 12 and 14 from cavity 20. Examples of useful phase control and/or attenuation elements might include an electro-optic modulator that imposes a modulation on the phase of the light and an attenuation element such as a Faraday rotator.

An optional enclosure or housing (not shown) provides an air tight seal for components within the housing, such as cavity 20, laser sources 12 and 14 and the various optical mirror elements such as to allow control of the environment within the housing and hence also the cavity 20. Enclosed cavities are desirable for certain applications. The optional enclosure may be made of any sutable, structurally stable material, such as a metal or metal alloy, or a plastic material.

In certain embodiments, CEOS system 10 also includes a temperature sensor positioned and configured to measure a temperature of the gas within cavity 20 and a pressure sensor positioned and configured to measure a pressure of the gas within cavity 20. It should be appreciated that more than one temperature sensor may be used, and that more than one pressure sensor may be used. For example, a single temperature sensor may be used to determine a temperature internal to the cavity, or where gas is flowed through the cavity, for example, two temperature sensors may be used to determine a temperature at a gas inflow port 22 and a gas exhaust port 24, from which a temperature of the gas in the cavity can be determined. In certain embodiments, the temperature and pressure of the gas in the cavity is controlled using a temperature control element and a pressure control element. Control of the ambient conditions, e.g., temperature and/or pressure, can be useful to help improve signal resolution and SNR.

Figure 2:
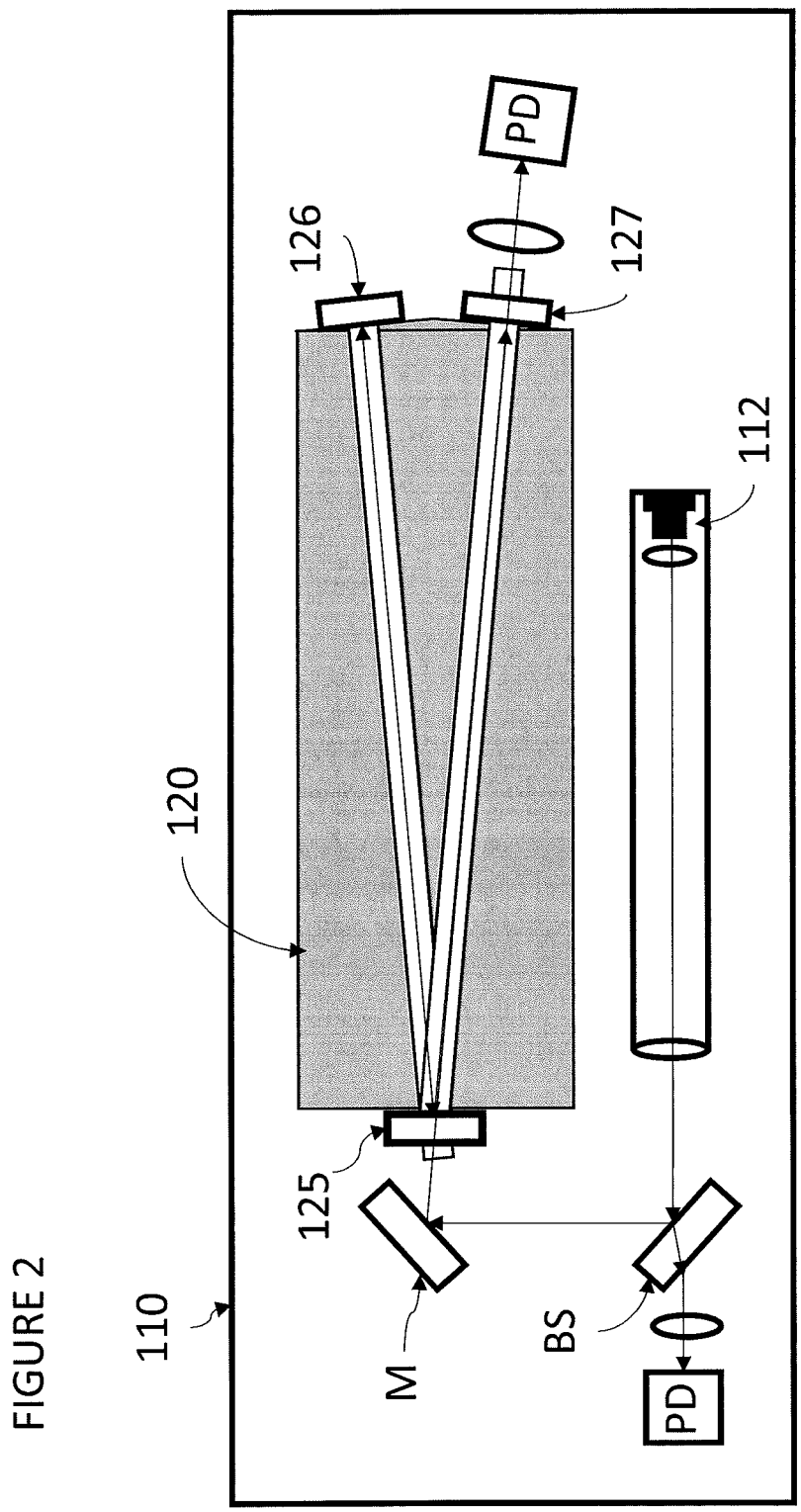
FIG. 2 shows an apparatus configuration according to another embodiment.

FIG. 2 shows a CEOS system 110 including a single laser, single resonant cavity configuration for measurement of trace gases in air, according to an embodiment. CEOS system 110 is particularly useful for measuring two trace gases. CEOS system 110 is similar to CEOS 10, but includes a single light source 112 that emits continuous wave coherent light, such as continuous wave laser light, and an optical cavity 120. A detector system (not shown) is provided and configured to measure absorption within the cavity, and hence an absorption coefficient, as well as other characteristics of incident and/or reflected light. In one embodiment, the detector system includes one or more detectors configured and arranged to measure optical signal emerging from one or more of the cavity mirrors. As shown, cavity 20 is a V-shaped cavity defined by cavity coupling mirror 125 and mirrors 126 and 127. One or more optical components, such as folding or directing mirrors (M) and/or lens elements, are configured and arranged to facilitate directing, and mode matching laser light from sources 112 to the optical cavity 120 via cavity coupling mirror 125. Optional beam splitting elements (BS) may be included. Depending on the frequency of incident light and the optical length of cavity 120 (e.g., optical length from mirror 127 to mirror 125 to mirror 126), light circulating in the cavity 120 may build up and resonate at one or a plurality of cavity modes (cavity resonances evenly separated in frequency; commonly known as the FSR or free spectral range of the cavity). A small portion of the intracavity light circulating in cavity 120 between mirror 127, 125 and 126, emerges or escapes via mirror 127 and also mirrors 126 and 125 as determined by their transmissivity. The light escaping mirror 125 is controlled by the various mirrors (M) and other optical elements to pass back to the source 112, e.g., for optical feedback. In certain aspects, light returning to sources may pass through optional phase control and/or attenuation elements, which advantageously provides for phase and/or intensity control of the optical feedback provided to source 112 from cavity 20. Examples of useful phase control and/or attenuation elements might include an electro-optic modulator that imposes a modulation on the phase of the light and an attenuation element such as a Faraday rotator.

Both the resonant cavity 120 and high reflectivity mirrors 125, 126 and 127 are made of the same material (e.g., fused silica). The design using fused silica was successfully implemented in a prototype. In certain embodiments, at least one of the folding mirrors and/or at least one of the beam shaping optical elements can also be made from the same material (or with a material with similar thermal expansion characteristics) as the mirrors and cavity, e.g. fused silica.

An optional enclosure or housing (not shown) provides an air tight seal for components within the housing, such as cavity 120, laser source 112 and the various optical elements such as to allow control of the environment within the housing and hence also the cavity 120. Enclosed cavities are desirable for certain applications.

In certain embodiments, system 110 also includes one or more temperature sensors positioned and configured to measure a temperature of the gas within cavity 120 and one or more pressure sensors positioned and configured to measure a pressure of the gas within cavity 120 as discussed above for FIG. 1. CEOS system 110 may also include temperature and/or pressure control elements as discussed above for FIG. 1.

In certain aspects, each source (e.g., 112 or 12 and 14) includes a laser or other coherent light source that is sensitive or responsive to optical feedback and that emits radiation at the desired wavelength(s) or desired wavelength range(s). One useful laser is a semiconductor diode laser that is sensitive to optical feedback from light impinging on the laser from the cavity coupling mirror (e.g., 25 or 125). Other laser sources might include diode lasers, quantum cascade lasers and solid state lasers. The reflectivities of the mirrors defining the cavity define the optical feedback intensity. U.S. Pat. No. 8,659,758, which is incorporated herein by reference in its entirety, discloses laser based cavity enhanced spectroscopy systems including mirror optimization techniques. It should be appreciated that the cavity coupling mirror (e.g., 25, 125) through which the laser light enters the cavity has a power reflectivity coefficient $R_1$ close to, but less than, unity such that the quantity $T=1-R_1$ is in the range from $10^{-1}$ to $10^{-5}$. The other cavity mirror(s) should have a power reflectivity $R_2$ equal to or lower than $R_1$. Such high reflective mirrors will certainly have some residual transmission, even though it may be as low as a few or several ppm.

In certain aspects, each source is capable of being frequency scanned, for example, a mean optical frequency of the laser is adjustable or tunable over a range of frequencies. This can be accomplished as is well known, such as, for example, by adjusting the current applied to a diode laser and/or adjusting a temperature of the laser medium. In certain aspects, the cavity (20 or 120) is also capable of being frequency scanned, e.g., by changing or adjusting an optical length of the cavity, whereby an optical frequency of a cavity resonance peak is adjustable over a range of frequencies. Adjustment of the optical length of the cavity can include adjusting a relative position of one or more of the cavity mirrors (e.g., using a piezo element), and/or adjusting a pressure of the medium within the cavity. An intelligence module or control module, such as a computer system, processor, ASIC or other control circuitry, is provided to enable automated control of the source frequency tuning or scanning and/or cavity optical length adjustment.

In certain embodiments, the CEOS system (10 or 110) is useful for detecting trace gases within a gas mixture present in the cavity. When the frequency of the incident light emitted by a source approaches the frequency of one of the cavity modes, the incident light entering the cavity begins to fill the cavity to that mode and may lock to that cavity mode. The optical intensity of the light circulating inside the resonance cavity reflects total cavity loss at the moment when the light frequency of incident light coincides with the cavity mode transmission peak. The total cavity loss is a sum of the cavity mirror losses and losses caused by absorption by the medium present in the cavity, e.g., absorption caused by absorbing analyte species present in the gaseous or liquid medium in the cavity. Examples of such species detectable by embodiments herein include $H_2O$, $N_2O$, $NO$, $NO_2$, $CO_2$, $CH_4$, various hydrogen, carbon, nitrogen and oxygen isotopes, and many others.

In various embodiments, the detector system is configured take measurements from which an absorption coefficient can be determined, e.g., based on measuring the intracavity optical power with and without an absorbing species present. For example, the power circulating inside the cavity ($P_{circ}$) is determined by the equation $P_{transm}=P_{circ}*T$, where T is the transmissivity of the mirror from which the light is escaping, and $P_{transm}$ is the power detected by the detector. A detector or detection element may be proximal to mirror element 27 or 127, for example. It should be appreciated that a detection element can additionally, or alternatively, be positioned to detect and measure the light escaping from mirror element 26 or 126 and/or mirror element 25 or 125 (e.g., reflected off of the backside of a beamsplitter (BS)). Also, a detection element could be configured and positioned internal to the cavity to measure the intracavity optical power. In certain embodiments, each detector element includes a photodetector, such as a photodiode, and associated electronics, for detecting light and outputting a signal representing the detected light. Examples of useful photodetectors might include silicon, InGaAs, Ge or GAP based photodetectors. Other useful detectors include CCDs, photomultipliers, etc. An intelligence module (e.g., a computer system, processor, ASIC or other control circuitry; not shown) receives the detector output signals and processes these signals to produce or generate a signal that characterizes the cavity loss based on the detection methodology used, e.g., PAS, free decay rate, phase shift, direct absorption, etc. For example, U.S. Pat. No. 8,659,759, which is incorporated herein by reference in its entirety, discloses laser based cavity enhanced spectroscopy systems including techniques for producing normalized signals that are a linear function of total cavity loss and that are not sensitive to laser-cavity coupling.

Additionally, as mentioned above, other detection methods can be used, for example, cavity ring-down spectroscopy methods, or cavity enhanced photo-acoustic spectroscopy (PAS) methods (see, e.g., U.S. Pat. No. 8,327,686, the contents of which are hereby incorporated by reference). Measurements made by the detector system are used to determine an absorption coefficient for any gas species or isotopes present in the cavity. For CRDS measurements, the ring-down decay time is measured and used to determine the absorption coefficient.

Figure 3:
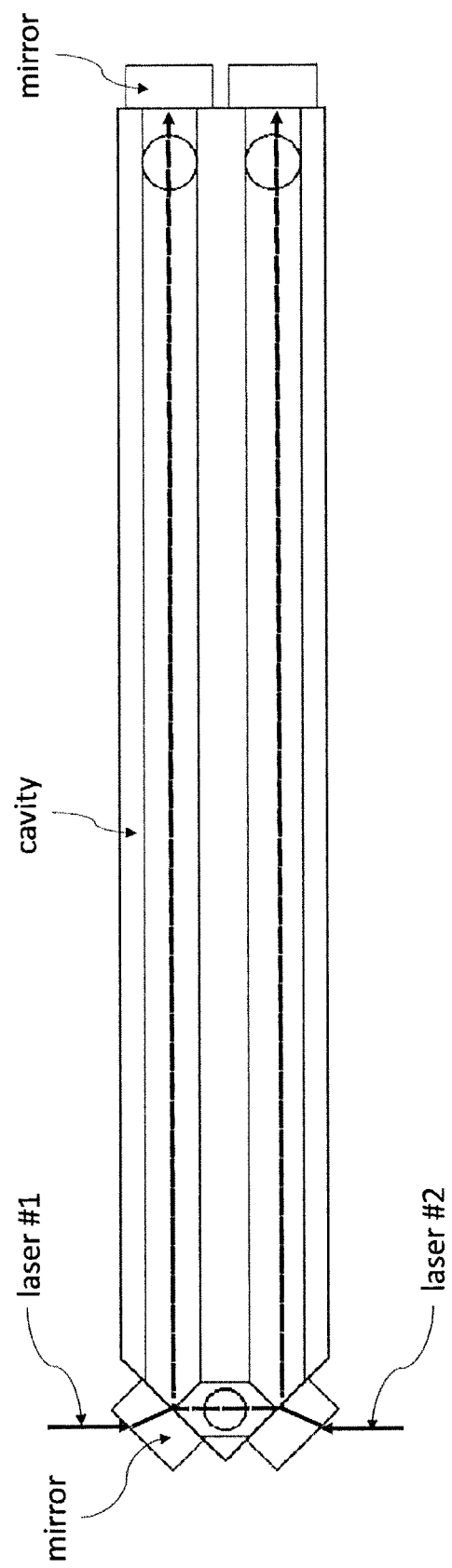
FIG. 3 shows an apparatus configuration with 4 mirrors according to an embodiment.
Figure 4:
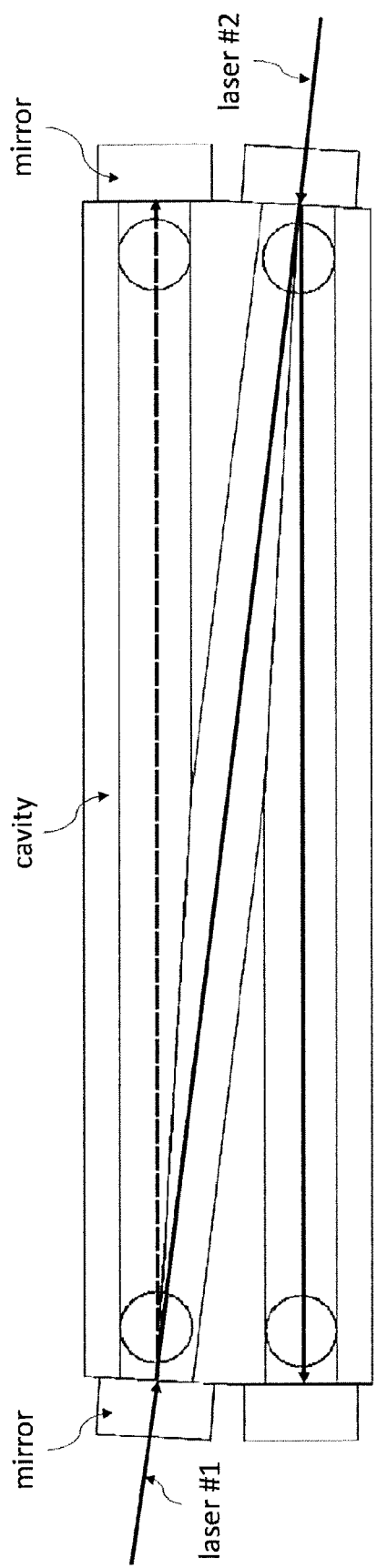
FIG. 4 shows an apparatus configuration with 4 mirrors according to another embodiment.

FIGS. 3 and 4 show apparatus configurations with 4 mirrors according to different embodiments. The various component and operating principles of the CEOS systems and cavities in FIGS. 3 and 4 are similar to those described above with reference to FIGS. 1 and 2, however an additional mirror element is provided. For example, in FIG. 3, an additional mirror element is provided and a linear cavity two arms is provided. Similarly, in FIG. 4, an additional mirror element is provided and a double-V-shaped cavity is provided. In FIGS. 3 and 4, both the resonant cavity and the high reflectivity mirrors are made of the same material (e.g., fused silica), or of materials having the same or similar coefficient of thermal expansion. In certain embodiments, additional components of each CEOS system, such as at least one of the folding mirrors and/or at least one of the beam shaping optical elements, can also be made from the same material (or with a material with similar thermal expansion characteristics) as the mirrors and cavity, e.g. fused silica.

Reference is also made to U.S. Pat. No. 8,659,758, U.S. Pat. No. 8,659,759, U.S. Pat. No. 8,885,167 and U.S. Pat. No. 8,665,442, which are each hereby incorporated by reference for all purposes, for gas analyzer systems and applications for which the present embodiments are useful.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed:

1. A resonant optical cavity system for detecting one or more analyte species present in a gaseous or liquid medium, comprising:
   a cavity body structure made of a first material, the cavity body structure having a first end and a second end;
   a first mirror element proximal to the first end of the cavity body structure;
   a second mirror element proximal to the second end of the cavity body structure;
   wherein the first mirror element and the second element define a cavity region therebetween, and wherein the first and second mirrors are made of a material having the same or a substantially similar coefficient of thermal expansion as the first material;
   a first laser that emits laser light;
   at least one optical element configured to direct the laser light of the first laser into the cavity region through the first mirror element; and
   a second laser that emits laser light, wherein the laser light of the second laser is directed into the cavity region through the second mirror element by the at least one optical element.

2. The resonant optical cavity system of claim 1, wherein the first material comprises a glass or a glass ceramic.

3. The resonant optical cavity system of claim 1, wherein the first and second mirrors are made of the first material.

4. The resonant optical cavity system of claim 1, wherein the first and second mirrors are made of a material different than the first material.

5. The resonant optical cavity system of claim 1, wherein the first material comprises fused silica.

6. The resonant optical cavity system of claim 1, further comprising a third mirror element proximal to the first or the second end, wherein the third mirror element is made of a material having the same or a substantially similar coefficient of thermal expansion as the first material.

7. The resonant optical cavity system of claim 6, further comprising a fourth mirror element proximal to the first or the second end, wherein the fourth mirror element is made of a material having the same or a substantially similar coefficient of thermal expansion as the first material.

8. The resonant optical cavity system of claim 7, wherein the third and fourth mirrors are high-reflectivity mirrors, each having a reflectivity of about 99% or greater on a surface facing an inside of the optical cavity body structure.

9. The resonant optical cavity system of claim 1, wherein the first and second mirrors are high-reflectivity mirrors, each having a reflectivity of about 99% or greater on a surface facing an inside of the optical cavity body structure.

10. The resonant optical cavity system of claim 1, wherein the first and second mirrors are high-reflectivity mirrors, each having a reflectivity of about 99.9% or greater on a surface facing an inside of the optical cavity body structure.

* * * * *